US008564310B2

(12) United States Patent
Yu et al.

(10) Patent No.: US 8,564,310 B2
(45) Date of Patent: Oct. 22, 2013

(54) CAPACITIVE OIL QUALITY MONITORING SENSOR WITH FLUORINATED BARRIER COATING

(75) Inventors: Steven Y. Yu, Austin, TX (US); Justin A. Riddle, St. Paul, MN (US); Naiyong Jing, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1100 days.

(21) Appl. No.: 12/542,829

(22) Filed: Aug. 18, 2009

(65) Prior Publication Data

US 2011/0043224 A1    Feb. 24, 2011

(51) Int. Cl.
*G01R 27/26* (2006.01)

(52) U.S. Cl.
USPC ........................................... 324/658

(58) Field of Classification Search
None
See application file for complete search history.

(56) References Cited

U.S. PATENT DOCUMENTS

| | | | |
|---|---|---|---|
| 3,739,265 A | 6/1973 | Skildum | |
| 3,746,974 A | 7/1973 | Stoakes et al. | |
| 4,082,997 A | 4/1978 | Ohtsu et al. | |
| 5,741,961 A | 4/1998 | Martin et al. | |
| 5,767,687 A | 6/1998 | Geist | |
| 5,818,731 A | 10/1998 | Mittal et al. | |
| 6,299,799 B1 | 10/2001 | Craig et al. | |
| 6,469,521 B1 | 10/2002 | Klün et al. | |
| 6,532,824 B1 | 3/2003 | Ueno et al. | |
| 6,600,306 B1 | 7/2003 | Pernot et al. | |
| 6,690,569 B1 | 2/2004 | Mayer et al. | |
| 6,822,461 B2 | 11/2004 | Klün | |
| 7,389,689 B2 | 6/2008 | Wargo | |
| 2005/0249942 A1 | 11/2005 | Coggio et al. | |
| 2006/0148971 A1 | 7/2006 | Jing et al. | |
| 2006/0216500 A1 | 9/2006 | Klün et al. | |
| 2006/0288877 A1 | 12/2006 | Chambon | |
| 2007/0277594 A1 | 12/2007 | Muhl et al. | |
| 2007/0286993 A1 | 12/2007 | Radcliffe et al. | |
| 2007/0287093 A1 | 12/2007 | Jing et al. | |
| 2008/0107907 A1 | 5/2008 | Coggio et al. | |
| 2008/0197065 A1* | 8/2008 | Wingo et al. | 210/198.2 |
| 2009/0029177 A1 | 1/2009 | Jing et al. | |
| 2009/0153155 A1* | 6/2009 | Chambon et al. | 324/698 |

FOREIGN PATENT DOCUMENTS

| | | |
|---|---|---|
| JP | 55-004531 | 1/1980 |
| WO | WO 2007/075803 A2 | 7/2007 |
| WO | WO 2009/140263 A2 | 11/2009 |

OTHER PUBLICATIONS

Fritsch, C., et at ; Changes in Dielectric Constant as a Measure of Frying Oil Deterioration; Journal of the American Oil CHemists' Society, 56, 746-750 (1979).
Dutt, N.V.K., Prasad, D.H.L., N.V.; Inter-relationships Among the Properties of Fatty Oils; Journal of the American Oil Chemists' Society, 66, 701 (1989).
International Search Report, PCTUS2010/045010, mailed Apr. 27, 2011, 4 pages.
Yu; U.S. Appl. No. 12/991,788, filed May 12, 2009.
Gonzales, U.S. Appl. No. 61/382,553, filed Sep. 14, 2010.

* cited by examiner

*Primary Examiner* — Jermele M Hollington
*Assistant Examiner* — Trung Nguyen
(74) *Attorney, Agent, or Firm* — Kenneth B. Wood (57) ABSTRACT

Methods and devices for evaluating the quality of oils are disclosed. The methods and devices can provide an indication of the oil quality based on the Total Polar Content of the oil. The methods rely on a reusable capacitive sensing element that comprises a fluorinated barrier coating, as disclosed herein.

26 Claims, 3 Drawing Sheets

CAPACITIVE OIL QUALITY MONITORING SENSOR WITH FLUORINATED BARRIER COATING

BACKGROUND

When oils (e.g. cooking oil, frying oil, fat, shortening, etc.) are exposed to high temperatures, oxidative reactions can take place that result in degradation of the oils. Thus, oil quality is often monitored e.g. in restaurant kitchens, so as to determine whether the oil is still suitable for use. A parameter often used to evaluate oil quality is the Total Polar (compound) Content of the oil. Various approaches (capacitive, spectroscopic, etc.) have been used for measuring the Total Polar Content of oils.

SUMMARY

Herein are disclosed methods and devices for evaluating the quality of oils. The methods and devices can provide an indication of the oil quality based on the Total Polar Content of the oil. The methods rely on a reusable capacitive sensing element that comprises a fluorinated barrier coating, as disclosed herein.

In one aspect, herein is disclosed a reusable capacitive sensing element for monitoring the total polar content of an oil sample, comprising: first and second interdigitated electrodes on a first major surface of a substrate, with first and second interdigitated electrodes being separated from each other by a gap therebetween that comprises exposed first major surface of the substrate; and, a fluorinated barrier coating atop the first and second interdigitated electrodes and the exposed major surface of the substrate therebetween.

In another aspect, herein is disclosed a method of monitoring the quality of a liquid oil sample, comprising bringing a sample of liquid oil and a reusable capacitive sensing element into contact with each other, wherein the reusable capacitive sensing element comprises: first and second interdigitated electrodes on a first major surface of a substrate, with first and second interdigitated electrodes being separated from each other by a gap therebetween that comprises exposed first major surface of the substrate; and, a fluorinated barrier coating atop the first and second interdigitated electrodes and the exposed major surface of the substrate therebetween; and, measuring a capacitive property of the interdigitated electrodes.

BRIEF DESCRIPTION OF THE DRAWINGS

These and other features and aspects of the present description will be more fully understood from the following detailed description of exemplary embodiments. It should be understood that the foregoing generalized descriptions and the following detailed descriptions are exemplary and are not restrictive of the present description.

Like reference numbers in the various figures indicate like elements. Certain elements may be present in identical multiples; in such cases a only single representative element may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Although terms such as "top", "bottom", "upper", "lower", "under", "over", "front", "back", "outward", "inward", "up" and "down", and "first" and "second" may be used in this disclosure, it should be understood that those terms are used in their relative sense only unless otherwise noted.

DETAILED DESCRIPTION

Figure 1:
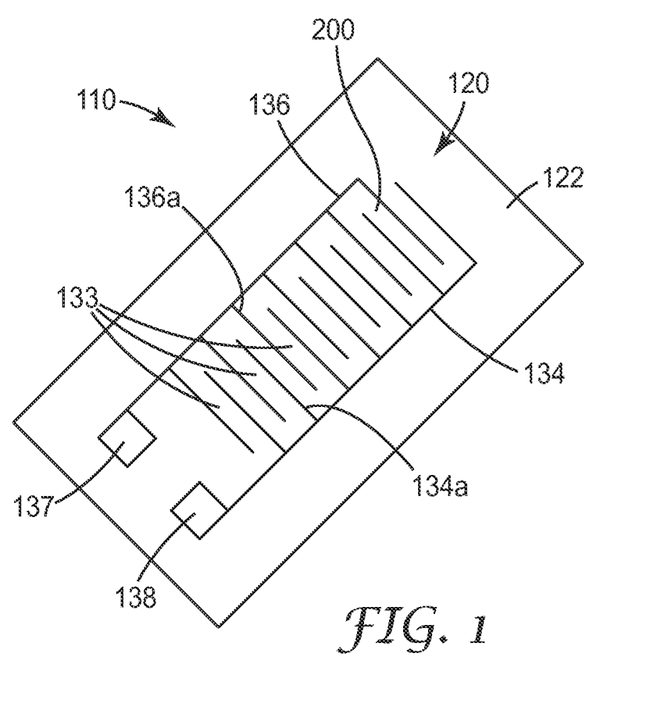
FIG. 1 is a perspective view of an exemplary capacitive sensing element with an exemplary fluorinated barrier coating.

Reference is made to FIG. 1, which shows a perspective view of an exemplary capacitive sensing element 110 which may be used in monitoring the quality of a liquid oil, e.g. cooking oil, frying oil, etc., such as may be used in restaurants and the like.

Capacitive sensing element 110 may be a generally planar, self-supporting element that carries a pair of electrically conductive pathways that together comprise capacitive electrodes, e.g., interdigitated electrodes 134 and 136, on one major surface 122 of substrate 120. The effect of an oil sample on a capacitive property (e.g., capacitance, impedance, etc.) of electrodes 134 and 136 may be measured and correlated with the Total Polar Content of the oil sample, thus allowing the oil quality to be ascertained.

Substrate 120 may be made of any suitable material that may carry electrical conductive pathways thereon without materially adversely affecting electrical measurements and that is sufficiently thermally and chemically stable to provide for the herein-disclosed uses. For example, substrate 120 may be made of a wide variety of materials, e.g. polymeric materials such as polyethylene terephthalate, polypropylene, polycarbonate, polytetrafluoroethylene, and the like. In various embodiments, substrate 120 may be flexible and thin, e.g. comprised of flex circuit material. In alternative embodiments, substrate 120 may be rigid (e.g., comprised of glass, silica, printed circuit board material, or the like).

Interdigitated electrode 134 and interdigitated electrode 136 are positioned on major surface 122 of substrate 120 in spaced configuration so as to together comprise interdigitated capacitive electrodes, according to methods well known in the art. Interdigitated electrodes 134 and 136 may be in generally coplanar alignment. Interdigitated electrodes 134 and 136 may be made by coating portions of surface 122 of substrate 120, such as by dip coating, screen printing, chemical vapor deposition, sputter coating, or other similar process, with conductive material to form a patterned continuous conductive trace (pathway). Such traces may also be provided by coating most or all of surface 122 with conductive material and then removing material except in areas where the conductive traces are left intact. Suitable conductive materials may include, but are not limited to, copper, gold, silver, aluminum, platinum, tin, carbon, or may be made of a composite of materials, and combinations thereof that are effective for performing in the manner desired. The conductive material may be provided directly atop an exposed surface of the material of which substrate 120 is comprised; or, the conductive material may be provided atop an exposed surface of layer of material (e.g. a tie layer, primer layer, adhesion-promoting layer, etc.) present upon substrate 120. Thus in this context, major surface 122 of substrate broadly encompasses any outermost exposed surface upon which the conductive materials that form interdigitated electrodes 134 and 136 are provided, whether such surface is an exposed surface of the material comprising the body of substrate 120, or an exposed surface of an additional layer thereon.

In various embodiments, the (lateral) width of the conductive trace may be on the order of about 10 microns to about 40 microns. In various embodiments, the thickness (depth) of the conductive trace may range from about 50 nm to about 1000 nm. In further embodiments, the thickness of the conductive trace may range from about 75 nm to about 250 nm.

Electrodes 134, 136 each comprise interdigitated fingers 134a and 136a respectively. In various embodiments, the interdigitated fingers of each electrode may have a pitch (i.e., spacing between fingers) on the order of about 10 microns to about 100 microns. In further embodiments, the pitch of each electrode may be about 15 to about 40 microns. In particular embodiments, the pitch may be about 20 microns to about 25 microns.

Gap (i.e., lateral space, along a plane generally parallel with major surface 122 of substrate 120) 133 is provided between adjacent portions of interdigitated fingers 134a and 136a of respective electrodes 134 and 136 as is illustrated in exemplary manner in FIG. 1. Gap 133 may be relatively constant (e.g. as shown in FIG. 1), or may vary as desired. In various embodiments, gap 133 may range from about 5 microns to about 20 microns (as measured at the closest point). In specific embodiments, gap 133 may be from about 10 microns to about 15 microns.

Capacitive sensing element 110 may be used by depositing a sample of the oil to be monitored, e.g. on major surface 122 of element 110 such that at least a portion of the oil sample overlies at least a portion of electrode 134 and of electrode 136. Alternatively, capacitive sensing element 110 may be dipped at least partially into an amount of the oil. Such dipping may be into a portion of oil which has been removed from a main oil container; or, element 110 may be dipped directly into a main oil container (e.g., a frying vat). The spacing, pitch, and overall dimension and layout of electrodes 134 and 136 may be such that an oil sample (e.g., that is applied to major surface 122 of substrate 120) covers sufficient area of electrodes 134 and 136 for successful measuring of an effect of the oil on a capacitive property of electrodes 134 and 136. While in the exemplary arrangement of FIG. 1 interdigitated electrodes 134 and 136 comprise rectilinear patterns (often called comb-style interdigitated patterns), other arrangements, such as interdigitated spiral patterns and the like, may be used.

Interdigitated electrodes 134 and 136 may be connected by leads to contact pads 138 and 137 respectively. Contact pads 137 and 138 are adapted to be electrically connectable to a testing apparatus that may be used in combination with element 110 for measuring the quality of an oil sample. Contact pads 137 and 138 and/or their leads may be supported on an extension of substrate 120 as illustrated in FIG. 1. Alternatively, (in a configuration not shown in FIG. 1), contact pads 137 and 138 may extend (protrude) longitudinally beyond an edge of substrate 120. Arrangements other than contact pads 138 and 137 may be used to achieve electrical connection between element 110 and the testing apparatus with which it is used, if desired.

The testing apparatus (not shown in any Figure) used with element 110 may include capacitance measuring circuitry and a mechanism (e.g. contact pads) for establishing electrical connection to interdigitated electrodes 134 and 136. The testing apparatus may additionally include a temperature control mechanism (e.g., a heating block), if it is desired to bring the oil sample and/or element 110 to a particular temperature for testing. The testing apparatus may additionally include control circuitry for operating the above-mentioned devices, for processing data received therefrom, for presenting the results of such processing to a user, for storing the data and/or results, for transmitting the data and/or results to a remote receiving location, and the like.

Capacitive sensing element 110 may optionally include an oil-permeable filter (not shown in any figure), positioned proximate major surface 122 of substrate 120, generally in overlapping relation with at least a portion of interdigitated electrodes 134 and 136, that may assist in preventing e.g. particles of debris from approaching interdigitated electrodes 134 and 136. Capacitive sensing element 110 may optionally include an oil absorbent pad, e.g. to receive and/or remove excess oil from the vicinity of interdigitated electrodes 134 and 136. Capacitive sensing element 110 may be supported by one or more layers, frames, etc., as necessary to provide enhanced mechanical integrity. For example, substrate 120 may comprise a relatively flexible polymeric substrate but may be attached to an underlying relatively rigid substrate (e.g., glass), so that surface 122 of substrate 120 that bears interdigitated electrodes 134 and 136 is exposed.

Capacitive sensing element 110 may be disposed after a single use if desired; however, as disclosed herein, it may be reusable and in at least some embodiments it may advantageously be used multiple times (e.g., five, ten, twenty, or more).

As disclosed herein, capacitive sensing element 110 comprises a fluorinated barrier coating 200 that covers interdigitated electrodes 134 and 136, and that additionally covers gap 133 therebetween. That is, fluorinated barrier coating 200 overlies the conductive material comprising interdigitated electrodes 134 and 136, and also overlies exposed surface 122 of substrate 120 in gap 133 between electrodes 134 and 136. Thus in typical use, an oil sample that is deposited on sensing element 110 for capacitance testing will reside on the outermost exposed surface of fluorinated barrier material 200 (or on the surface of any optional layer that may be present atop fluorinated barrier material 200).

In some embodiments, fluorinated barrier coating 200 may cover electrodes 134 and 136 while leaving contact pads 137 and 138 uncovered (e.g., so that electrical contact between contact pads 137 and 138 and the testing apparatus is facilitated). This arrangement can be obtained e.g. by not applying fluorinated barrier coating 200 atop contact pads 137 and 138. Alternatively, it can be obtained e.g. by coating fluorinated barrier coating 200 atop the entirety of major surface 122 of substrate 120 and then removing (e.g., by physically abrading, chemically etching, etc.) fluorinated barrier coating 200 from at least a portion of contact pads 137 and 138. In some embodiments, fluorinated barrier material 200 may overlie fingers 134a and 136a of electrodes 134 and 136 while leaving the conductive trace that connects these fingers to each other and/or to their respective contact pads uncovered, as may be achieved by the above-described selective application of fluorinated barrier coating 200, and/or selective removal of fluorinated barrier coating 200 in desired areas.

Figure 3:
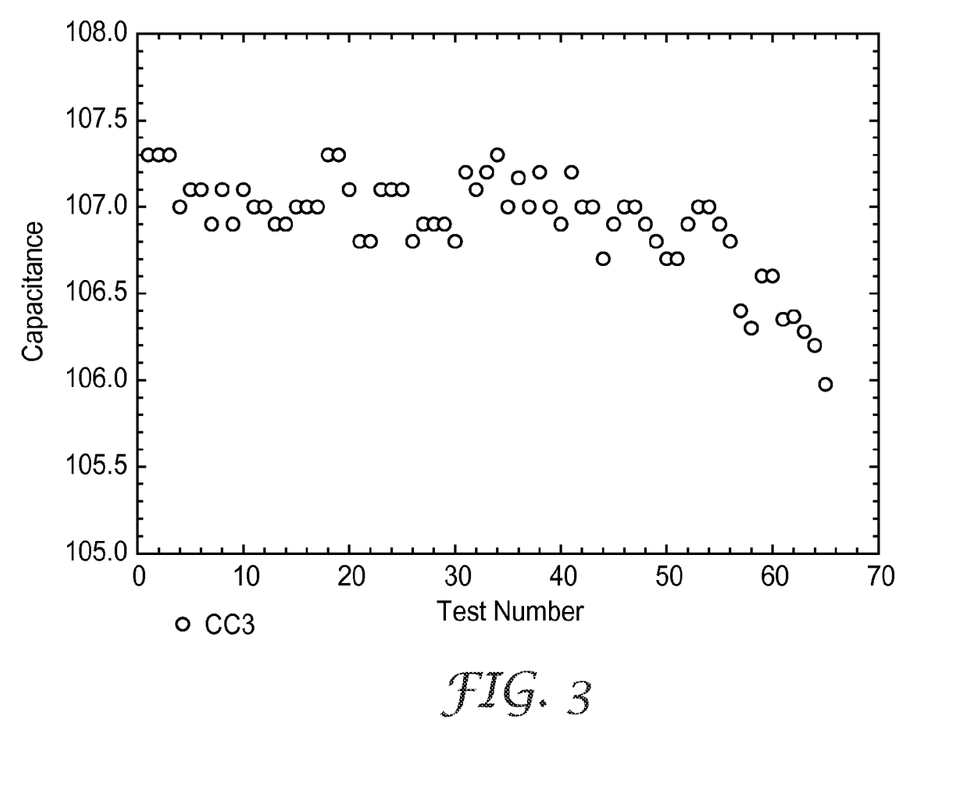
FIG. 3 shows capacitance of an exemplary capacitive sensing element comprising an exemplary fluorinated barrier coating, over multiple successive exposures of the sensing element to oil samples.

The inventors have discovered that fluorinated barrier coating 200 may provide several advantages in at least some embodiments disclosed herein. Fluorinated barrier coating 200 may provide a mechanically durable coating that may allow element 110 to be reused multiple times. Such reuse typically necessitates an oil sample to be physically removed (e.g., wiped away) from element 110 (e.g., to be removed from interdigitated electrodes 134 and 136 and from surface 122 (or the surface of any tie layer or other layer thereon) of substrate 120 in gap 133), after each use, so that any residual oil is sufficiently low in quantity as to not unacceptably affect the accuracy of the measuring of a later oil sample. The inventors have found that, in the absence of fluorinated barrier coating 200, such physical removal of an oil sample, even if carefully done, may affect the interdigitated electrodes (e.g., by physically abrading or removing a portion of the conductive material) such that the accuracy of a subsequent measurement is altered. The providing of fluorinated barrier coating 200 as disclosed herein, may reduce this phenomenon to the point that multiple (e.g., as many as fifty) oil samples may be successively tested with a single reusable element 110 before element 110 is discarded, as evidenced by the discussion of FIG. 3 in the Examples section. While not wishing to be limited by theory or mechanism, the inventors postulate that the high oleophobicity (e.g., oil-repellence) of fluorinated barrier coating 200, combined with the mechanical strength and thickness of the coating, may render it relatively easy to remove residual oil from the surface of coating 200 without damaging (abrading, etc.) coating 200 and/or the conductive material thereberneath.

The inventors have further surprisingly found that fluorinated barrier coating 200 may provide other benefits beyond the above-mentioned oil repellency. That is, when provided as disclosed herein, fluorinated barrier coating 200 may comprise sufficient water-barrier properties to advantageously enhance the functioning of element 110. This advantage results from the inventors' discovery of an unappreciated source of a problem with using capacitive sensing elements (without any type of barrier coating thereon) to monitor oil samples. Specifically, the inventors noted the problem of high variability in the course of repeated capacitance measurements (e.g., as evidenced by data set labeled "Comparative" of FIG. 2 of the Examples). The source of this problem was unknown until the inventors discovered that heating of such sensing elements (e.g., in a convection oven at 80-90° C. for approximately one hour) between successive capacitance measurements served to reduce the variability. Without wishing to be limited by theory or mechanism, the inventors postulate that this variability may be caused by water that may be present in the oil (and/or may be present in an atmosphere to which the sensing element is exposed). The inventors postulate that even very small amounts of such water that may migrate to the surface of interdigitated electrodes 134 and 136 may alter subsequent capacitance measurements, and surmise that such heating may drive such water away from electrodes 134 and 136.

The inventors have found that, surprisingly, fluorinated barrier coating 200 sharply reduces the variability of capacitance measurements (as evidenced in FIG. 2 of the Examples, by comparison of data sets CC3 and FPC1 with the Comparative data set), to the point that such (cumbersome and lengthy) heating steps may no longer be needed in order to obtain acceptably low variability. Again without wishing to be limited by theory or mechanism, the inventors postulate that this may be achieved at least partially by the ability of fluorinated barrier coating 200 to prevent water (e.g. whether in the form of individual water molecules, water vapor, clusters of water molecules, water droplets, etc.) from penetrating through coating 200 and reaching the surface of the conductive material of interdigitated electrode 134 or 136.

In addition to the aforementioned advantages, the inventors have found that fluorinated barrier coating 200 may act to at least partly prevent particles (e.g., debris such as food residue and the like) from coming sufficiently close to adjacent fingers 134a and 136a of electrodes 134 and 136 respectively so as to establish a sufficiently conductive pathway therebetween so as to affect that measured capacitance of the electrodes (e.g., so as to cause a short circuit between the two electrodes). In earlier work, the inventors had found it helpful, or even necessary, in some cases, to provide a filter to prevent such particles from approaching electrodes 134 and 136. While such a filter may be optionally used in the present case, the inventors have found that fluorinated barrier coating 200 may provides sufficient protection against such effects of particles, that such a filter may not be required.

The inventors have found that fluorinated barrier coating 200 may provide additional benefits. Specifically, when an oil sample is deposited onto the portion of element 110 comprising electrodes 134 and 136 with fluorinated barrier coating 200 present thereon, the relatively low surface energy of barrier coating 200 (due to its fluorine content), may provide that any spreading (e.g., wicking) of the oil may be limited such that it does not reach contact pads 137 or 138 and thus may not be likely to interfere with the electrical connections between element 110 and the testing apparatus with which it is used. In various embodiments, fluorinated barrier coating 200 may comprise a surface energy of less than about 30 dynes/cm, less than about 25 dynes/cm, less than about 20 dynes/cm, or less than about 15 dynes/cm. In certain embodiments, fluorinated barrier coating 200 comprises a surface energy of from about 10 dynes/cm to about 30 dynes/cm.

The inventors have found that fluorinated barrier coating 200, of thickness, barrier properties, mechanical durability, etc., sufficient to provide the above-discussed advantages, can be provided without coating 200 unsatisfactorily affecting the measuring of capacitance (e.g., without coating 200 having such a large effect on the capacitance of interdigitated electrodes 134 and 136 that any effect of an oil sample on the capacitance is obscured). Fluorinated barrier coating 200 can be comprised of any fluorinated material that comprises sufficient oil and water repellency, oil and water barrier properties, mechanical strength and integrity, and durability, to provide the above-discussed advantages, while not unacceptably affecting the measuring of capacitance.

Fluorinated barrier layer 200 as defined herein comprises a thickness of greater than 100 nm (0.10 microns). In various embodiments, the thickness of fluorinated barrier layer 200 may be at least about 0.2 microns, at least about 0.5 microns, or at least about 1.0 microns. In further embodiments, the thickness of fluorinated barrier layer 200 may be at most about 12 microns, at most about 8 microns, or at most about 4 microns.

Fluorinated barrier layer 200 is further defined herein as comprising a total fluorine content of at least about 0.05 percent by weight. By total fluorine content is meant the amount of fluorine in relation to the entire (dry, e.g. after removal of any coating solvent) composition of the coating. In various embodiments, the total fluorine content may be at least about 0.5 percent, at least about 5.0 percent, or at least about 20 percent, by weight.

To provide the herein-described barrier properties, fluorinated barrier coating 200 should not comprise sufficient microscopic or macroscopic porosity to allow water, etc. to penetrate therethrough, and should further be free of pinholes or other such defects as might allow water to penetrate. In specific embodiments, fluorinated barrier coating 200 comprises a nonporous material.

In various embodiments, fluorinated barrier coating 200 may comprise a crosslinked material. Coating 200 may in such case comprise e.g. the reaction product of a fluorinated molecule that comprises one or more reactive groups which can react to form a high molecular weight material, e.g. comprising a network structure.

Coating 200 may be obtained from the reaction product of at least one fluorinated unsaturated compound (that may, e.g., polymerize by a free-radical mechanism). In some embodiments, coating 200 may comprise the reaction product of molecules that comprise, in the same molecule, fluorine atoms (e.g., in $CF_3$ groups, larger fluorinated alkyl groups, and the like) and acrylate and/or methacrylate groups (such molecules will be referred to herein as fluorinated/(meth)acrylate molecules). In various embodiments, the fluorinated groups may comprise terminal groups, pendant groups, side-chain groups, and the like; or they may comprise segments (e.g., backbone segments) located in between two or more terminal (meth)acrylate groups. In some embodiments the reaction product may be only of fluorinated/(meth)acrylate molecules with fluorinated/(meth)acrylate molecules. However, in some cases it may only be necessary to include an amount of fluorinated/(meth)acrylate molecules (and/or a level of fluorine atoms in such molecules) to provide the above-listed advantages. Thus in some embodiments, the reaction product may be of fluorinated/(meth)acrylate molecules with (meth)acrylate molecules that are not fluorinated, which may be advantageous in view of the expense of such fluorinated molecules.

Coating compositions as used herein may be obtained by combining certain nonfluorinated (meth)acrylate molecules with fluorinated (meth)acrylate molecules to form a coating composition. Suitable fluorinated (meth)acrylate molecules (e.g., perfluoroalkyl (meth)acrylate molecules, as well as suitable nonfluorinated (meth)acrylate molecules, are described e.g. in U.S. Patent Application Publication 2007/0286993 to Radcliffe et al., which is incorporated by reference herein for this purpose.

Coating compositions as used herein may also be obtained by including fluorinated/(meth)acrylate molecules in e.g. (meth)acrylate-based coating compositions which may have been developed for other purposes. Such coating compositions may comprise e.g. fillers such as inorganic particles, nanoparticles, etc., if such fillers impart desirable properties (e.g., durability and the like), and may further comprise additives, initiators, crosslinking agents (which may be fluorinated or nonfluorinated), coupling agents, stabilizers, and the like as is well known in the art. Suitable coating compositions and reaction products thereof, comprising fluorinated/(meth) acrylate molecules, and methods of depositing and reacting (curing) such materials, are described e.g. in U.S. Patent Application Publication 2007/0286993 to Radcliffe et al. which is herein incorporated by reference for this purpose. Another suitable coating composition to which fluorinated/ (meth)acrylate molecules may be added is found in Example 3 of U.S. Pat. No. 6,299,799 to Craig et al.

Coatings thus formed by such reaction products will typically comprise at least linear high molecular weight fluorinated materials (after being reacted). If the molecules used are multifunctional (e.g., comprising more than one (meth)acrylate group), the coating may comprise a network rather than substantially linear polymer chains. Often, the reaction product will comprise fluorine atoms bonded to substituents of the chain backbones (e.g., in the case of (meth)acrylate molecules in which fluorine atoms are typically not found directly bonded to the reactive C=C bond).

In particular embodiments, at least some of the fluorinated/ (meth)acrylate molecules comprise perfluoropolyether (meth)acrylate molecules. As used herein "perfluoropolyether (meth)acryl molecule" refers to a molecule comprising at least one perfluoropolyether group and at least one (meth) acryl group typically joined by a linking group. Perfluoropolyether (meth)acryl molecules can be represented by the following Formula I:

$$(R_f)—[(W)—(R_A)]_w \qquad \text{(Formula I)}$$

wherein $R_f$ is perfluoropolyether group; W is a linking group; and $R_A$ is a (meth)acryl group or —COCF=$CH_2$; and w is 1 or 2.

The perfluoropolyether group $R_f$ can be linear, branched, cyclic, or combinations thereof and can be saturated or unsaturated. The perfluoropolyether has at least two catenated oxygen heteroatoms. Exemplary perfluoropolyethers include, but are not limited to, those that have perfluorinated repeating units selected from the group of —($C_pF_{2p}$)—, —($C_pF_{2p}$O)—, —(CF(Z))—, —(CF(Z)O)—, —(CF(Z)$C_pF_{2p}$O)—, —($C_pF_{2p}$CF(Z)O)—, —($CF_2$CF(Z)O)—, or combinations thereof. In these repeating units, p is typically an integer of 1 to 10. In some embodiments, p is an integer of 1 to 8, 1 to 6, 1 to 4, or 1 to 3. The group Z is a perfluoroalkyl group, perfluoroether group, perfluoropolyether, or a perfluoroalkoxy group, all of which can be linear, branched, or cyclic. The Z group typically has no more than 12 carbon atoms, no more than 10 carbon atoms, or no more than 9 carbon atoms, no more than 4 carbon atoms, no more than 3 carbon atoms, no more than 2 carbon atoms, or no more than 1 carbon atom. In some embodiments, the Z group can have no more than 4, no more than 3, no more than 2, no more than 1, or no oxygen atoms. In these perfluoropolyether structures, the different repeat units can be distributed randomly along the chain.

$R_f$ can be monovalent or divalent. In some molecules where $R_f$ is monovalent, the terminal groups can be ($C_pF_{2p+1}$)—, ($C_pF_{2p+1}$O)—, (X'$C_pF_{2p}$O)—, or (X'$C_pF_{2p+1}$)— where X' is hydrogen, chlorine, or bromine and p is an integer of 1 to 10. In some embodiments of monovalent $R_f$ groups, the terminal group is perfluorinated and p is an integer of 1 to 10, 1 to 8, 1 to 6, 1 to 4, or 1 to 3. Exemplary monovalent $R_f$ groups include $CF_3O(C_2F_4O)_nCF_2$—, and $C_3F_7O(CF(CF_3)CF_2O)_nCF(CF_3)$— wherein n has an average value of 0 to 50, 1 to 50, 3 to 30, 3 to 15, or 3 to 10.

Suitable structures for divalent $R_f$ groups include, but are not limited to, —$CF_2O(CF_2O)_q(C_2F_4O)_nCF_2$—, —($CF_2)_3O(C_4F_8O)_n(CF_2)_3$—, —$CF_2O(C_2F_4O)_nCF_2$—, and —$CF(CF_3)(OCF_2CF(CF_3))_sOC_tF_{2t}O(CF(CF_3)CF_2O)_nCF(CF_3)$—, wherein q has an average value of 0 to 50, 1 to 50, 3 to 30, 3 to 15, or 3 to 10; n has an average value of 0 to 50, 3 to 30, 3 to 15, or 3 to 10; s has an average value of 0 to 50, 1 to 50, 3 to 30, 3 to 15, or 3 to 10; the sum (n+s) has an average value of 0 to 50 or 4 to 40; the sum (q+n) is greater than 0; and t is an integer of 2 to 6.

As synthesized, molecules according to Formula I may include a mixture of $R_f$ groups. The average structure is the structure averaged over the mixture components. The values of q, n, and s in these average structures can vary, as long as the compound has a number average molecular weight of at least about 400. Compounds of Formula I often have a molecular weight (number average) of 400 to 5000, 800 to 4000, or 1000 to 3000.

The linking group W between the perfluoropolyether segment and (meth)acryl or —COCF=$CH_2$ endgroup may include a divalent group selected from an alkylene, arylene, heteroalkylene, or combinations thereof and an optional divalent group selected from carbonyl, carbonyloxy, carbonylimino, sulfonamido, or combinations thereof. W can be unsubstituted or substituted with an alkyl, aryl, halo, or combinations thereof. The W group typically has no more than 30 carbon atoms. In some compounds, the W group has no more than 20 carbon atoms, no more than 10 carbon atoms, no more than 6 carbon atoms, or no more than 4 carbon atoms. For example, W can be an alkylene, an alkylene substituted with an aryl group, or an alkylene in combination with an arylene.

Perfluoropolyether (meth)acrylate molecules can be synthesized by known techniques such as described in U.S. Pat. Nos. 3,553,179 and 3,544,537 and 7,101,618. Further details of perfluoropolyether (meth)acrylate molecules can be found in U.S. Patent Application Publication 2005/0249942 to Coggio et al., incorporated by reference herein for this purpose.

In further embodiments, at least some of the fluorinated/(meth)acrylate molecules comprise perfluoropolyether urethane (meth)acrylate molecules. Such molecules may be made for example by first reacting a polyisocyanate with a perfluoropolyether molecule (e.g., of the type described above) containing an alcohol, thiol, or amine group. The perfluoropolyether urethane additive may then be combined with a (e.g. non-fluorinated) isocyanate reactive multifunctional free-radically polymerizable (meth)acrylate crosslinker. Other methods are possible as is known in the art.

A variety of polyisocyanates may be utilized. "Polyisocyanate" means any organic compound that has two or more reactive isocyanate (—NCO) groups in a single molecule such as diisocyanates, triisocyanates, tetraisocyanates, etc., and mixtures thereof. Cyclic and/or linear polyisocyanate molecules may be used. The polyisocyanate(s) of may be aliphatic or aromatic. One or more isocyanate reactive perfluoropolyethers (for example, perfluoropolyether alcohols, perfluoropolyether amines, and the like), can be used in the preparation of the perfluoropolyether urethane material.

An exemplary perfluoropolyether urethane (meth)acrylate molecules is shown as follows:

(Formula 2)

In the above, "HFPO" represents a perfluoropolyether as described in further detail in PCT Published Application WO 2009/029438 to Pokorney et al. This document describes perfluoropolyether urethane (meth)acrylate molecules, the preparation thereof, and the preparation of coating compositions and reaction products thereof, and is incorporated by reference herein for this purpose. Still further details of such materials are described in U.S. Patent Application Publication 2006/0216500 to Klun et al., which is also incorporated by reference herein for this purpose.

The perfluoropolyether urethane (meth)acrylate materials described herein may be the only fluorinated material employed in the coating composition, or may be used in combination with various other fluorinated materials having at least one moiety selected from fluoropolyether, fluoroalkyl, and fluoroalkylene linked to at least one free-radically reactive group (e.g., a (meth)acrylate group). When such a second fluorinated material employed, it may be preferred that such second fluorinated compound also comprises an HFPO-moiety. Various fluorinated materials that can be employed in combination with the perfluoropolyether urethane polymeric material described are described in U.S. Patent Application Publication 2006/0216500 to Klun et al.

In the above embodiments, the (meth)acrylate molecules (whether fluorinated or not) can be monofunctional (i.e., bearing a single (meth)acrylate group), or multifunctional (i.e. bearing two or more (meth)acrylate groups). The term (meth)acrylate means a molecule that comprises at least one acrylate group and/or at least one methacrylate group. In describing these materials, the term "compound" means a collection of molecules of the described type.

While it is often convenient to use the above-described (meth)acrylate systems to form fluorinated barrier coating 200, other systems (whether relying on free radical polymerization, or some other reaction mechanism), can be used. For example, fluorinated vinyl compounds (e.g., fluorinated vinyl ethers and the like), which are well known to those in the art, may be used. Or, fluorinated epoxy compounds can be used, again as known in the art.

Thus in summary, fluorinated barrier coating 200 may be made by the reaction of any suitable reactive compounds that comprise fluorine atoms. Such fluorine atoms may be present in fluorinated alkyl groups (that are, e.g., pendant groups of a reactive monomer or oligomer). Such groups might include e.g. $CF_3$, $C_2F_5$, $C_3F_7$, $C_4F_9$, $C_5F_{11}$, $C_6F_{13}$, $C_7F_{15}$, $C_8F_{17}$, as well as the above-described perfluoropolyethers and the like.

The above compositions can be applied to substrate 120 and to electrodes 134 and 136 thereon and to exposed surface 122 of substrate 120 (or to any tie layer, protective layer, or other layer present on substrate 120) in gap 133, by any known method including dip coating, roll coating, slot coating, die coating and the like. Such coatings may also be applied by vapor-condensation methods such as those outlined in U.S. Pat. No. 5,877,895. The coatings may be cured by means well known in the art, e.g., by radiation, thermal exposure, etc., depending on the particular initiator, curing agent, etc. used.

In various embodiments, fluorinated barrier coating 200 may comprise a fluorinated polymeric material (that is, a high molecular weight, generally linear material). Such materials may comprise relatively few or no covalent crosslinks (e.g., may not be the product of a reaction mixture of molecules with multiple reactive groups), but may e.g. comprise sufficiently high molecular weight to (e.g., by the forming of a semicrystalline structure in which microcrystallites within the material act as physical crosslinks) be capable of forming a mechanically durable coating with barrier properties acceptable for the uses disclosed herein. In the context herein, a high molecular weight polymeric material means that the material has a molecular weight of at least 5,000. In particular embodiments, such fluorinated polymeric materials may comprise fluorine atoms which are directly attached to atoms of the polymer backbone (e.g., the polymeric material may comprise —$CF_2$— groups in the polymer backbone).

Fluorinated polymeric materials which may be suitable may include e.g. poly (tetrafluoroethylene). Materials obtained from the polymerization of e.g. vinyl fluoride, perfluoropropylene, vinylidine fluoride, chlorotrifluoroethylene, perfluorinated vinyl ethers, and the like, and copolymers of these with each other and/or with tetrafluoroethylene, may also be used. Such materials may include e.g. those products known as THV (copolymers of tetrafluoroethylene, hexafluoropropylene, and vinylidine fluoride), ETFE (copolymers of tetrafluoroethylene and ethylene), FEP (copolymer of TFE and hexafluoropropylene), PFA (copolymer of tetrafluoroethylene and perfluoro(propoxy vinyl ether)). Blends of the above homopolymers and/or copolymers may be used. These and other suitable materials are described in further detail in U.S. Patent Application Publication 2009/0029177 to Jing et al., which is incorporated by reference herein for this purpose.

Blends and/or copolymers of the above fluorinated materials with nonfluorinated materials may also be used.

In various embodiments, the fluorinated polymeric material may comprise a fluorine content of at least about 25 wt. %, or at least about 59 wt. %. In further embodiments, the fluorinated polymeric material may comprise a fluorine content of at most about 78.5 wt. %, or at most about 65 wt. %.

Suitable fluorinated polymeric materials may comprise materials that are relatively soluble in common organic solvents (as exemplified, e.g., by the product available from Dyneon LLC of Oakdale, Minn., under the trade designation THV-220D). Such materials may be relatively soluble due to their composition, relatively low crystallinity, relatively low molecular weight, or combinations of these attributes, as is well understood by those of skill in the art. Thus, in various embodiments coating 200 may be formed by the deposition of such a fluorinated polymeric material onto substrate 120, e.g., by the coating of such a polymer in solution followed by the removal of the coating solvent.

Suitable fluorinated polymeric materials may also comprise materials that are relatively insoluble in common organic solvents (e.g., poly(tetrafluoroethylene). Such materials may be relatively insoluble due to their composition, relatively high crystallinity, relatively high molecular weight, or combinations of these attributes, again as is well understood by those of skill in the art. Even if insoluble, such materials may be available as coatable dispersions of particles. Thus, in various embodiments coating 200 may be formed by the deposition of a high molecular weight fluorinated polymer that is in the form of a dispersion in a carrier (e.g., a dispersion in an organic solvent, an aqueous latex, etc.), followed by the removal of the carrier (possibly followed by at least some degree of coalescence of the particles).

In certain embodiments, coating compositions can be achieved that are solution-dispersions comprising a relatively soluble fluorinated polymeric material dissolved in a solvent, and further comprising dispersed particles of relatively insoluble fluorinated polymeric material (an example of such an approach is coating composition FPC1 discussed in the Examples). Such compositions can be coated as desired and the coated composition may optionally be subjected to further treatments (e.g., heating, physical rubbing, etc.) to aid in spreading and/or coalescing the fluorinated particles. Further details of such solution-dispersion coating compositions, and methods of applying such coating compositions to substrates, is found in U. S. Patent Application Publication 2006/0148971 to Jing et al., incorporated by reference herein for this purpose.

In some embodiments, the fluorinated polymeric material may bond (e.g., covalently bond) to the conductive material of electrodes 134 and 136, to surface 122 of substrate 120 in gap 133 therebetween, or both. In such cases, coupling agents and the like may be used to enhance such bonding. Suitable coupling agents are described e.g. in U.S. Patent Application Publication 20090029177 to Jing et al. (and may also be used in combination with the aforementioned fluorinated/(meth) acrylates). In other embodiments, such bonding may not occur, and fluorinated barrier coating 200 may be held in place by physical forces. In some embodiments, fluorinated barrier coating 200 may bond preferentially to conductive material of electrodes 134 and 136, and may be held in place in gap 133 primarily by the physical strength of coating 200 rather than by any bond to substrate 120. Conversely, in other embodiments fluorinated barrier coating 200 may bond preferentially to surface 122 of substrate 120 and may be held in place over electrodes 134 and 136 primarily by the physical strength of coating 200 rather than by an bond to the conductive material.

Coatings comprising such high molecular weight fluorinated polymeric materials may be distinguished in general from coatings derived from the earlier-described reaction products in that the fluorinated polymeric materials are generally already at their final high molecular weight before being deposited upon substrate 120. In contrast, the earlier-described materials are often coated as solutions or syrups containing relatively low molecular weight monomers, oligomers and the like, and are then reacted in place. Combinations of both materials may of course be used. And, even with high molecular weight polymeric materials, some small amount of crosslinking may still occur (whether by design or adventitiously). Fluorinated high molecular weight polymeric materials may at least in some cases also be distinguishable from e.g. (meth)acrylate-derived coatings in that the fluorinated polymeric materials often comprise fluorine atoms bonded directly to carbon atoms of main chains of the polymer (e.g., as exemplified by poly(tetrafluoroethylene). Of course, some materials (e.g. those derived from monomers such as certain fluorinated vinyl ethers) may comprise fluorine atoms attached both to carbons of the main polymer chain and to substituents thereof.

The above discussions are provided only in order to illustrate the various fluorinated materials that may be used herein, and one of ordinary skill in the art will appreciate that the boundaries between these descriptive categories may not always be distinct. For example, in some embodiments, fluorinated barrier coating 200 may be achieved from the reaction product of (relatively high molecular weight) fluoropolymers which comprise reactive functionality, and multifunctional (meth)acrylates, wherein the components are present in phases which form a co-crosslinked interpenetrating polymer network. Such approaches are described in further detail in U.S. Patent Application Publication 2008/0107907 to Coggio et al., which is incorporated by reference herein for this purpose. One of ordinary skill will also appreciate that combinations of any or all of the herein-described materials may be used.

Other methods of providing fluorinated barrier coating 200 may also be used, including e.g. plasma polymerization of suitable fluorine-containing materials, and the like.

EXAMPLES

Preparation of Fluorinated Reactive Compositions

Perfluoropolyether Urethane Acrylate Composition 1 (PUAC1)

A perfluoropolyether urethane acrylate composition was prepared in similar manner as described in U.S. Patent Application Publication 2006/0216500, under Preparation No. 5. (Nomenclature used in these examples corresponds to that used in the '500 document). The formulation corresponded to Preparation 5.4 in Table 1 of the '500 document (DES N100/0.67 PET3A/0.33 HFPO—C(O)NHCH$_2$CH$_2$OH). The composition was made at 50% total solids by weight in MEK.

Perfluoropolyether Urethane Acrylate Composition 2 (PUAC2)

A perfluoropolyether urethane methacrylate composition was prepared in similar manner as described above. The formulation corresponded to (DES N100/0.90 PET3A/0.15 HFPO—C(O)NHCH$_2$CH$_2$OH). The composition was made at 65% total solids by weight in acetone.

Non-Fluorinated Acrylate Composition 1 (NFAC1)

A nonfluorinated acrylate composition was obtained similar to that described in Example 3, U.S. Pat. No. 6,299,799.

Fluorinated Methacrylate Composition 1 (FMAC1)

A fluorinated methacrylate monomer (2-(N-Ethylperfluoroalkylsulfonamido) ethyl methacrylate) was obtained from 3M Company, St. Paul, Minn., under the trade designation Fluorad FX-14.

Coating compositions were prepared by combining various quantities (listed in grams) of the above compositions, as outlined in Table 1.

TABLE 1

| Coating Composition | NFAC1 (g) | PUAC1 (g) | PUAFC2 (g) | FMAC1 (g) | MEK (g) |
|---|---|---|---|---|---|
| 1 | 7.6 | 0.40 | — | — | 32 |
| 2 | 3.8 | 0.20 | — | — | 16 |
| 3 | 3.8 | 0.20 | — | — | 16 |
| 4 | 1.9 | 0.10 | — | — | 18 |
| 5 | 2.8 | 0.15 | — | — | 17 |
| 6 | 3.8 | — | 0.15 | — | 16 |
| 7 | 3.8 | — | 0.075 | — | 16 |
| 8 | 7.5 | — | — | 0.5 | 32 |

Interdigitated electrodes were prepared by coating gold (or, in some cases, copper) conductive traces onto pieces of polyester films. Each sensing element comprised a pair of interdigitated electrodes of the general design shown in FIG. 1. The total combined area of the two electrodes was approximately 0.2 square inches. The pitch spacing for each electrode was approximately 20 microns and the space between adjacent electrodes was approximately 10 microns. Each electrode comprised a contact pad.

Coated Sensing Element Set 1

A glass vessel was charged with Coating Composition 1. Capacitive sensing elements were submerged vertically into the solution (sufficiently deep to cover the interdigitated electrodes while leaving the contact pads untouched) and removed by a motor driven apparatus. Individual elements were removed from the coating solution at rates of 3.5 feet per minute, 2.5 feet per minute, or 1.25 feet per minute. All samples were then allowed to air dry for 15 minutes. They were then irradiated by being passed through a UV curing unit (Fusion UV Systems Inc., Model MC-6RQN, equipped with "D" bulbs). Four passes through the UV curing unit were performed at a rate of 30 feet per minute.

Coated Sensing Element Set 2

Samples were coated with Coating Compositions 2-7, in similar manner as in Coated Sensing Element Set 1, except that the sensing elements were submerged in the coating solution manually and removed manually at a rate estimated to be approximately 3 feet per minute.

Coated Sensing Element Set 3

Samples were coated with Coating Composition 8, in similar manner as in Coated Sensing Element Set 1, except that the interdigitated electrodes were comprised of copper traces, and that the sensing elements were submerged in the coating solution manually and removed manually at a rate estimated to be approximately 3 feet per minute. The coated sensing elements were air dried for 10 minutes at room temperature and were then placed in an oven for 3 minutes at 80° C. and then UV cured (4 passes 30 ft/min with D-bulb).

In all cases, the thickness of the fluorinated barrier coating was estimated to be about one to four microns.

Preparation of High Molecular Weight Fluorinated Polymer Compositions

Fluorinated Polymer Composition 1 (FPC1)

A coating composition was prepared in the following manner. An aqueous dispersion (at 20 wt. %) of fluoropolymer was obtained from Dyneon LLC, Oakdale, Minn., under the trade designation THV-220D. This fluoropolymer is a copolymer of polymer of tetrafluoroethylene, hexafluoropropylene and vinylidene fluoride and is relatively soluble in organic solvents such as MEK. An aqueous dispersion (at 60 wt. %) of fluoropolymer was obtained from Dyneon LLC under the trade designation TF-5032R. This fluoropolymer is comprised of poly(tetrafluoroethylene) (PTFE) and is relatively insoluble in organic solvents such as MEK. The dispersions were combined in proportions to provide an 80:20 ratio of THV-220D fluoropolymer to PTFE, on a dry weight basis, and were then precipitated with $MgCl_2$ by the methods outlined in U.S. Patent Application Publication 2006/0148971. The precipitated, solid material was then added to MEK at 10 wt. % followed by shaking at room temperature. In this manner was obtained a solution-dispersion with the THV-220D fluoropolymer present primarily as a solution in MEK, and the PTFE present primarily as a dispersion of particles. A mixture of 3-aminopropyltrimethoxysilane (10 wt. % in MeOH) was then combined with the fluoropolymer dispersion-solution at a ratio of 95:5 fluoropolymer dispersion-solution:silane mixture. The resulting mixture was then diluted with MEK to provide coating composition FPC1, at approximately 2 wt. % solids.

Coated Sensing Element Set 4

Capacitive sensing elements similar to those described above were coated with composition FPC1. A glass vessel was charged with Coating Composition FPC1. Capacitive sensing elements were submerged vertically into the solution (sufficiently deep to cover the interdigitated electrodes while leaving the contact pads untouched) and removed by a motor driven apparatus. Individual elements were removed from the coating solution at rates of 3.5 feet per minute. All samples were then allowed to air dry for 15 minutes and were then placed in an oven at 120° C. for 15 minutes. The thickness of the fluorinated barrier coating was estimated to be about one to four microns. The diameter of the PTFE particles (estimated at approximately 160 nm) appeared to be sufficiently small that the coating surface was generally smooth.

Testing of Capacitive Sensing Elements with Fluorinated Barrier Coatings

Various samples from the above sets were placed horizontally with the interdigitated electrodes and fluorinated barrier coating facing upward. Mixtures of canola oil and soybean oil were placed on portions of the sensing element that had been coated with the fluorinated barrier coating. Little or no spreading of the oil sample was observed. In contrast, oil samples that were deposited on uncoated portions of the sensing elements were observed to spread, in some cases so as to cover the contact pads of the interdigitated electrodes.

Figure 2:
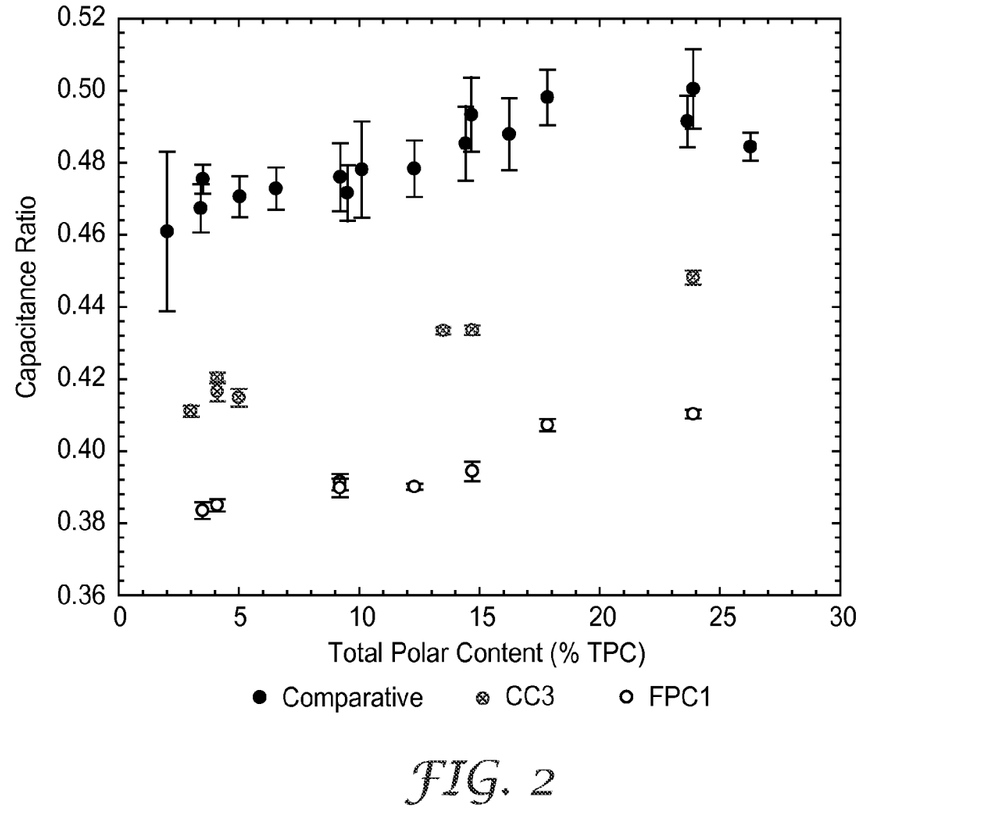
FIG. 2 shows capacitance ratio as a function of Total Polar Content, obtained with exemplary capacitive sensing elements comprising exemplary fluorinated barrier coatings.

Representative samples from the above sets were tested for their response to oil. Oil samples were prepared with various amounts of Total Polar Content (as determined by column chromatography). The sensing elements were placed horizontally with the interdigitated electrodes and fluorinated barrier coating facing upward. A custom built testing apparatus was electrically connected to the contact pads of each electrode and was used to monitor the capacitance of the electrodes (impedance spectroscopy, as performed by use of a Solartron frequency response analyzer, was also used to ensure that the custom built testing apparatus was working properly). Capacitance values were recorded in the absence of oil. An oil sample (of volume approximately 0.3 cc) was placed upon the surface of the sensing element, such that it covered at least a portion of each interdigitated electrode. Capacitance values were recorded in the presence of oil. The Capacitance Ratio (defined as the capacitance value without oil, minus the capacitance value in the presence oil; divided by the capacitance value without oil) was obtained. Results are presented in FIG. 2, for a sample from Coated Sensing Element Set 2 that had been coated with Coating Composition 3 (data are labeled CC3). Results are also presented in FIG. 2, for a sample from Coated Sensing Element Set 4 that had been coated with Fluorinated Polymer Composition 1 (data labeled FPC1). Results are also presented in FIG. 2 (data labeled Comparative), for electrodes which did not have a fluorinated barrier coating. For all data sets, each data point in FIG. 2 is an average of at least 10 repeated exposures of an individual electrode to oil samples of a given Total Polar Content. The repeated measurements were obtained by physically removing (by wiping with a microfiber cloth) an oil sample after capacitance measurement, and then depositing another sample from the same batch of oil and measuring the capacitance, and so on. For each data point, the vertical distance between the error bars represents the variability between the individual measurements, as represented by the standard deviation.

A representative sample from Coated Sensing Element Set 2, coated with Coating Composition 3, was obtained and was repeatedly tested for capacitance value, in similar manner as described above. After testing, the oil sample was removed by wiping with a microfiber cloth and a fresh sample from the same batch of oil was then deposited. The capacitance so obtained (in picoFarads) is presented in FIG. 3.

The tests and test results described above are intended solely to be illustrative, rather than predictive, and variations in the testing procedure can be expected to yield different results. All quantitative values in the Examples section are understood to be approximate in view of the commonly known tolerances involved in the procedures used. The foregoing detailed description and examples have been given for clarity of understanding only. No unnecessary limitations are to be understood therefrom.

It will be apparent to those skilled in the art that the specific exemplary structures, features, details, configurations, etc., that are disclosed herein can be modified and/or combined in numerous embodiments. All such variations and combinations are contemplated by the inventor as being within the bounds of the conceived invention. Thus, the scope of the present invention should not be limited to the specific illustrative structures described herein, but rather by the structures described by the language of the claims, and the equivalents of those structures. To the extent that there is a conflict or discrepancy between this specification and the disclosure in any document incorporated by reference herein, this specification will control.

What is claimed is:

1. A reusable capacitive sensing element for monitoring the total polar content of an oil sample, comprising:
    first and second interdigitated electrodes on a first major surface of a substrate, with first and second interdigitated electrodes being separated from each other by a gap therebetween that comprises exposed first major surface of the substrate; and,
    a fluorinated barrier coating atop the first and second interdigitated electrodes and the exposed major surface of the substrate therebetween,
    wherein the fluorinated barrier coating comprises a reaction product of at least one perfluoropolyether (meth) acrylate compound that comprises at least one terminal $F(CF(CF_3)CF_2O)aCF(CF_3)$— group and at least two (meth)acrylate groups; and wherein a averages from 4 to 15.

2. The sensing element of claim 1, herein the fluorinated barrier coating comprises fluorinated groups chosen from the group consisting of $CF_3$, $C_2F_5$, $C_3F_7$, $C_4F_9$, $C_5F_{11}$, $C_6F_{13}$, $C_7F_{15}$, $C_8F_{17}$, and perfluoropolyethers, and combinations thereof.

3. The sensing element of claim 1, wherein the fluorinated barrier coating comprises a reaction product of at least one fluorinated (meth)acrylate compound with at least one non-fluorinated (meth)acrylate compound.

4. The sensing element of claim 1 wherein the coating comprises a total fluorine content of at least about 0.5 percent by weight.

5. The sensing element of claim 1 wherein the coating comprises a total fluorine content of at least about 5.0 percent by weight.

6. The sensing element of claim 1 wherein the fluorinated barrier coating comprises a high molecular weight fluorinated polymeric material.

7. The sensing element of claim 1 wherein the thickness of the fluorinated barrier coating is from about 0.5 microns to about 10 microns.

8. The sensing element of claim 1 wherein the thickness of the fluorinated barrier coating is from about 1.0 microns to about 4 microns.

9. The sensing element of claim 1 wherein the fluorinated barrier coating comprises a surface energy of from about 10 dynes/cm to about 30 dynes/cm.

10. A reusable capacitive sensing element for monitoring the total polar content of an oil sample, comprising:
    first and second interdigitated electrodes on a first major surface of a substrate, with first and second interdigitated electrodes being separated from each other by a gap therebetween that comprises exposed first major surface of the substrate; and,
    a fluorinated barrier coating atop the first and second interdigitated electrodes and the exposed major surface of the substrate therebetween,
    wherein the fluorinated barrier coating comprises a reaction product of at least one perfluoropolyether urethane (meth)acrylate compound.

11. The sensing element of claim 10 wherein the perfluoropolyether urethane (meth)acrylate compound comprises:

12. The sensing element of claim 10 wherein the coating comprises a total fluorine content of at least about 0.5 percent by weight.

13. The sensing element of claim 10 wherein the coating comprises a total fluorine content of at least about 5.0 percent by weight.

14. The sensing element of claim 10 wherein the fluorinated barrier coating comprises a high molecular weight fluorinated polymeric material.

15. The sensing element of claim 10 wherein the thickness of the fluorinated barrier coating is from about 1.0 microns to about 4 microns.

16. The sensing element of claim 10 wherein the fluorinated barrier coating comprises a surface energy of from about 10 dynes/cm to about 30 dynes/cm.

17. The sensing element of claim 10 wherein the gap between the first and second interdigitated electrodes is no more than about 20 microns.

18. The sensing element of claim 10 wherein each interdigitated electrode comprises fingers with a pitch of no more than about 20 microns.

19. The sensing element of claim 10 wherein the fluorinated barrier coating comprises a reaction product of at least one perfluoropolyether urethane (meth)acrylate compound with at least one nonfluorinated (meth)acrylate compound.

20. A reusable capacitive sensing element for monitoring the total polar content of an oil sample, comprising:

first and second interdigitated electrodes on a first major surface of a substrate, with first and second interdigitated electrodes being separated from each other by a gap therebetween that comprises exposed first major surface of the substrate; and, a fluorinated barrier coating atop the first and second interdigitated electrodes and the exposed major surface of the substrate therebetween, wherein the fluorinated barrier coating comprises a high molecular weight fluorinated polymeric material that comprises fluorine atoms directly attached to backbone atoms of the polymer chains comprising the polymeric material.

21. The sensing element of claim 20 wherein the high molecular weight fluorinated polymeric material is chosen from the group consisting of poly(tetrafluoroethylene), poly(hexafluoropropylene), poly(vinylidine fluoride), and copolymers and blends thereof.

22. The sensing element of claim 20, wherein the fluorinated barrier coating further comprises a reaction product of at least one fluorinated (meth)acrylate compound.

23. The sensing element of claim 20 wherein the high molecular weight fluorinated polymeric material comprises a fluorine content of at least about 25 percent by weight.

24. The sensing element of claim 20 wherein the coating comprises a total fluorine content of at least about 5.0 percent by weight.

25. The sensing element of claim 20 wherein the thickness of the fluorinated barrier coating is from about 0.5 microns to about 10 microns.

26. The sensing element of claim 20 wherein the fluorinated barrier coating comprises a surface energy of from about 10 dynes/cm to about 30 dynes/cm.

* * * * *

UNITED STATES PATENT AND TRADEMARK OFFICE
CERTIFICATE OF CORRECTION

PATENT NO.         : 8,564,310 B2                                     Page 1 of 1
APPLICATION NO.    : 12/542829
DATED              : October 22, 2013
INVENTOR(S)        : Steven Yong Yu et al.

It is certified that error appears in the above-identified patent and that said Letters Patent is hereby corrected as shown below:

Title Page, References Cited – Column 2 (Other Publications)
Line 1, Delete "at" and insert -- al --, therefor.

In the Claims
Column 16
Line 7, In Claim 2, delete "herein" and insert -- wherein --, therefor.

Signed and Sealed this
Eleventh Day of March, 2014

Michelle K. Lee
*Deputy Director of the United States Patent and Trademark Office*